United States Patent
Bolz

(10) Patent No.: US 6,861,850 B2
(45) Date of Patent: Mar. 1, 2005

(54) DEVICE FOR MEASURING THE INTERNAL RESISTANCE OF A LINEAR LAMBDA PROBE

(75) Inventor: Stephan Bolz, Pfatter (DE)

(73) Assignee: Siemens Aktiengesellschaft, Munich (DE)

( * ) Notice: Subject to any disclaimer, the term of this patent is extended or adjusted under 35 U.S.C. 154(b) by 91 days.

(21) Appl. No.: 10/320,109

(22) Filed: Dec. 16, 2002

(65) Prior Publication Data

US 2003/0127323 A1 Jul. 10, 2003

Related U.S. Application Data

(63) Continuation of application No. PCT/DE01/02138, filed on Jun. 8, 2001.

(30) Foreign Application Priority Data

Jun. 16, 2000 (DE) .......................................... 100 29 795

(51) Int. Cl.[7] .............................................. G01R 27/08
(52) U.S. Cl. ........................ 324/691; 324/693; 324/713
(58) Field of Search .............................. 73/118.1, 31.05; 204/425, 426; 324/428, 430, 442, 691, 713, 693

(56) References Cited

U.S. PATENT DOCUMENTS

| | | | |
|---|---|---|---|
| 4,419,190 A | 12/1983 | Dietz et al. ................. 204/1 T |
| 4,505,783 A | 3/1985 | Mase et al. .................. 204/1 T |
| 5,091,698 A | * | 2/1992 | Grabs .......................... 324/693 |
| 5,106,481 A | * | 4/1992 | Rankin et al. .............. 204/426 |
| 6,073,083 A | * | 6/2000 | Schnaibel et al. ............ 702/65 |
| 6,259,259 B1 | * | 7/2001 | Raffalt et al. ............... 324/650 |
| 6,763,697 B2 | * | 7/2004 | Bolz .......................... 73/23.2 |

FOREIGN PATENT DOCUMENTS

| | | | |
|---|---|---|---|
| DE | 3117790 A1 | 11/1982 | ............ G01K/7/26 |
| DE | 3835852 A1 | 4/1990 | ............ G01K/7/26 |
| DE | 3836045 A1 | 4/1990 | ........... G01R/27/16 |
| DE | 3903314 A1 | 8/1990 | ........... G01R/27/14 |
| DE | 19636226 A1 | 3/1998 | ............ F02D/41/14 |

OTHER PUBLICATIONS

Microelectronics Second Edition, Jakob Millman P.H.D., Arvin Grabel, S.C.D., 1987; PP. 698–702.

* cited by examiner

*Primary Examiner*—N. Le
*Assistant Examiner*—Walter Benson
(74) *Attorney, Agent, or Firm*—Baker Botts L.L.P.

(57) ABSTRACT

A device for measuring the internal resistance (Ris) of a linear lambda probe (S) of an internal combustion engine is disclosed. The device comprises a voltage amplifier (V6) for amplifying an alternating voltage (VOSZ), which declines to the internal resistance (Ris) and which is induced by an alternating current applied to the first probe terminal Vs+. The inventive device also comprises a synchronous demodulator (V7) for rectifying the amplified alternating voltage (VEIN) and a successive filtering whose amplification factor can be switched over with the frequency of the alternating voltage (VOSZ).

14 Claims, 5 Drawing Sheets

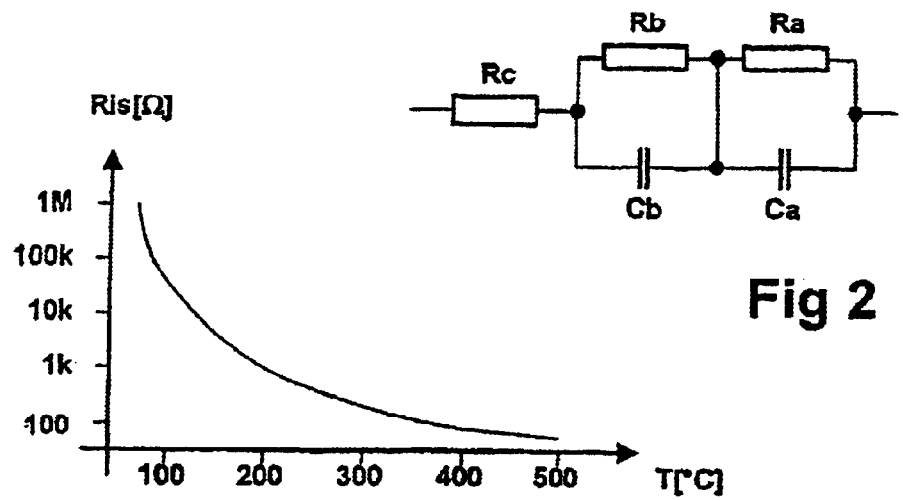
Fig 1
Fig 2
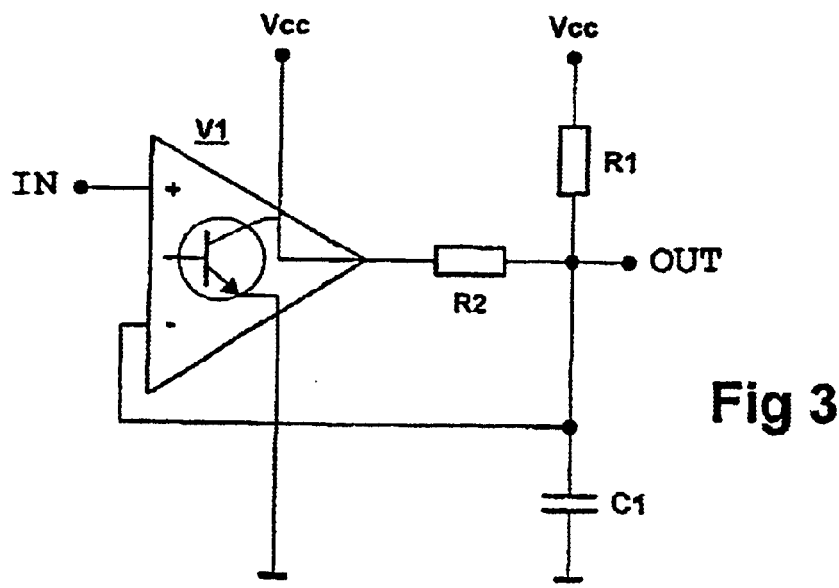
Fig 3

DEVICE FOR MEASURING THE INTERNAL RESISTANCE OF A LINEAR LAMBDA PROBE

CROSS REFERENCE TO RELATED APPLICATION

This application is a continuation of copending International Application No. PCT/DE01/02138 filed Jun. 8, 2001, which designates the United States, and claims priority to German Application DE10029795.1 filed Jun. 16, 2000.

BACKGROUND OF THE INVENTION

The invention relates to a device for measuring the internal resistance of a linear lambda probe of an internal combustion engine.

The dynamic resistance of the diffusion barrier of a linear lambda probe which is arranged in the exhaust tract of an internal combustion engine in order to determine the fuel/air mixture fed to the internal combustion engine has a temperature dependence which leads to errors in the transmission ratio, i.e. in the measurement result. This is countered by measuring the probe temperature and adjusting it to a constant value by means of a heating element installed in the lambda probe. For reasons of cost, a separate thermal element is not used for temperature measurement here, and instead the highly temperature dependent internal resistance Ris of the lambda probe is measured.

A customary measurement method for determining the internal resistance Ris is to apply to the probe an alternating current which has been acquired by means of a square wave oscillator. An alternating voltage then drops across the internal resistance Ris. This alternating voltage is amplified and rectified and can be fed to a microprocessor for adjusting the temperature.

This measurement method results in a falsification of the output signal with a roof-shaped slope of the square wave signal (for example owing to excessively small coupling capacitors or effects of the probe control loop), and there is a high degree of sensitivity to EMC interference due to the rapid response of the rectifier.

SUMMARY OF THE INVENTION

The object of the invention is to provide a device for measuring the internal resistance of a linear lambda probe by means of which more precise measurement of the internal resistance is made possible and in which the measurement error which arises during the rectification of the alternating voltage signal and the sensitivity to electromagnetic interference pulses are reduced.

This object can be achieved according to the invention by means of a device for measuring the internal resistance of a linear lambda probe of an internal combustion engine, having a voltage amplifier for amplifying an alternating voltage which drops across the internal resistance and is brought about by an alternating current applied to the first probe terminal, and having a rectifier for rectifying the amplified alternating voltage, wherein the rectifier is a synchronous demodulator whose voltage amplification can be switched between two predefined values with the frequency of the alternating voltage which drops across the internal resistance, and whose output signal is filtered by means of a filter.

A switch can be switched with the frequency of the alternating voltage which drops across the internal resistance and which is arranged between the non-inverting input of the synchronous demodulator and the second probe terminal. The predefined values of the voltage amplification of the synchronous demodulator can be values "+1" and "−1".

Another embodiment is a circuit for measuring the internal resistance of a linear lambda probe comprising a voltage amplifier coupled with a resistance which receives a signal having a frequency, a synchronous demodulator receiving the output signal of the amplifier, wherein the voltage amplification of the demodulator is switched between two predefined values according to the frequency of the signal.

The circuit may further comprise a filter for filtering the output signal of the demodulator. The voltage amplifier can be a differential amplifier. The demodulator may comprise an operational amplifier. The operational amplifier can be coupled with the amplifier through a first and second resistance. The predefined values may be "1" and "−1", respectively. The circuit may further comprise a switch between a noninverting input of the operational amplifier and a bias voltage. The filter may comprise a resistance and a capacitance coupled in series between the output of the demodulator and a reference potential. The bias voltage can be derived from the lambda probe and can be a mid voltage.

Yet another embodiment according to the present invention is an arrangement for determining the fuel/air mixture comprising a lambda probe having at least a first and second terminal, an amplifier having an input coupled with the first and second terminal and an output, a signal generator for generating a signal having a frequency being fed to the first input of the lambda probe, and a rectifier having an input coupled with the output of the amplifier and an output, wherein the rectifier comprises a demodulator having a selectable amplification which is switched between a first and second value with a frequency controlled by the frequency of the signal.

The arrangement may further comprise a filter for filtering the output signal of the demodulator. The demodulator can comprise an operational amplifier. The first and second values may be "1" and "−1", respectively. The arrangement may further comprise a switch between a noninverting input of the operational amplifier and the second terminal. The filter can comprise a resistance and a capacitance coupled in series between the output of the demodulator and a reference potential.

BRIEF DESCRIPTION OF THE DRAWINGS

An exemplary embodiment of the invention is described in more detail below with reference to a schematic drawing, in which:

FIG. 1 shows a diagram of the dependence of the probe internal resistance Ris on the temperature, FIG. 2 shows an equivalent circuit diagram of the internal resistance Ris, FIG. 3 shows a basic circuit diagram of a peak value rectifier.

DETAILED DESCRIPTION OF THE PREFERRED EMBODIMENTS

An equivalent circuit diagram of a probe internal resistance Ris of a lambda probe whose temperature-dependence is illustrated in FIG. 1 can be represented as a complex reactance composed of the series connection of a first resistor Ra, in parallel with which a first capacitor Ca is connected, a second resistor Rb, in parallel with which a second capacitor Cb is connected, and a third resistor Rc, see FIG. 2.

Here, Ra/Ca represents the contact resistance between electrodes and ceramic material (the time constant τa=Ra*Ca is typically approximately 10 ms), Rb/Cb: represents the transition between the grain boundaries of the ceramic synthetic grains (the time constant τb=Rb*Cb is typically approximately 100 μs), and Rc: represents the intrinsic resistance of the sintered material.

The resistance Ra is highly dependent on aging and can therefore not be used for measuring temperature. The series connection of Rb/Cb and Ra gives rise to a resistance value of approximately 100 Ω given a measuring frequency of 3 kHz. This is the probe internal resistance Ris to be measured.

In the customary measurement method already mentioned for determining the probe internal resistance Ris, the probe has an alternating current—for example 500 μAss (peak-to-peak) applied to it. An alternating voltage of 500 μAss*100 Ω=50 mVss is introduced at the internal resistance Ris. This alternating voltage is amplified and rectified and can then be fed to a microprocessor for regulating the temperature.

Figure 5:
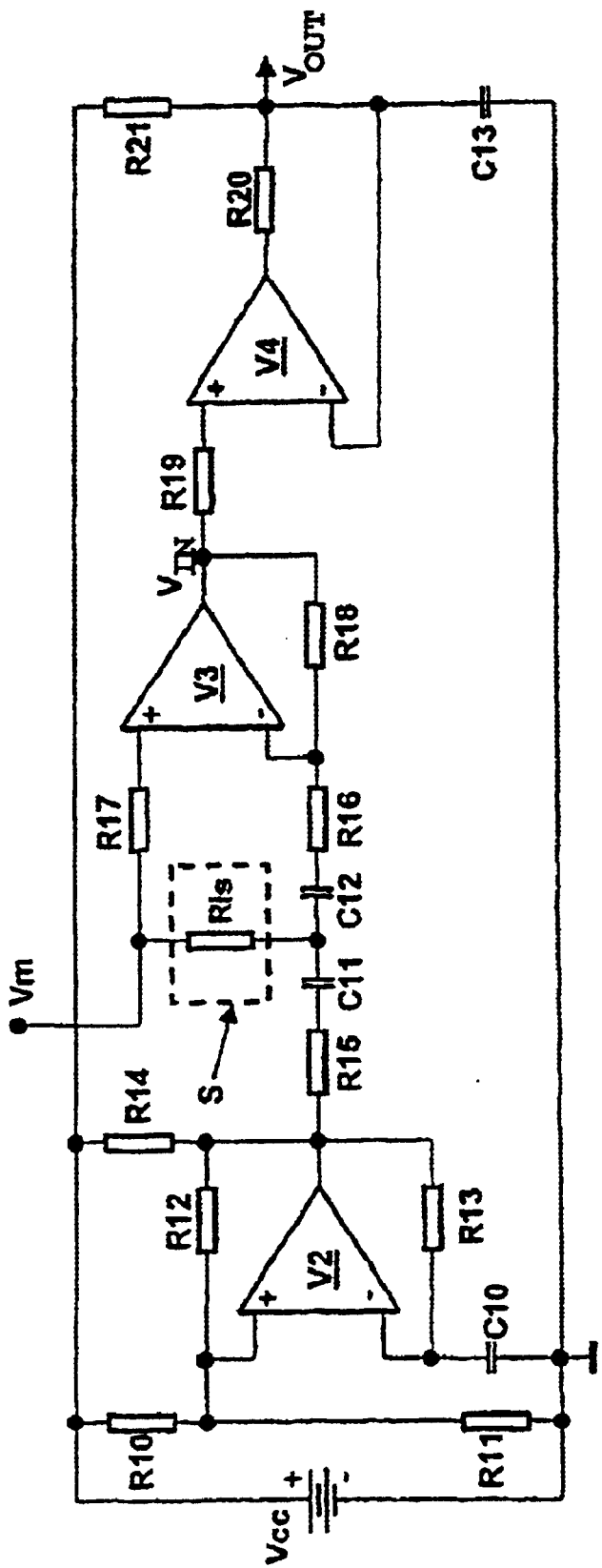
FIG. 5 shows a basic circuit diagram of a known circuit for determining the probe internal resistance Ris with a peak value rectifier.

The alternating current is generated, for example, by means of a 3 kHz square wave oscillator which is supplied with Vcc=5 V. The signal is fed to the probe via a high impedance resistor (10 kΩ) and a decoupling capacitor. FIG. 5 shows a known typical circuit design for doing this, which will be explained later.

In the known circuit a peak value rectifier for converting the alternating voltage signal into a DC voltage is used and it is illustrated in a basic circuit diagram in FIG. 3.

It will be assumed, for example, that a DC voltage Vm=2.5 V is present at the input IN. The comparator V1 operates as an isolation amplifier and therefore the voltage at the output OUT is also 2.5 V. This is achieved in that the capacitor C1 charges slowly via the resistor R1. As long as the voltage at the output OUT is lower than the voltage at the input IN, the output transistor of the comparator V1 remains non-conductive.

If the output voltage exceeds the input voltage, the transistor switches on and discharges the capacitor C1 via resistor R2 until the output voltage is below the input voltage again. The transistor then becomes non-conductive again and the output voltage rises, driven slowly again by the charge current of R1.

An oscillation around $V_{OUT}$=Vm is produced. It is important here that the time constant for charging ($\tau_{charge}$=R1*C1) and for discharging ($\tau_{discharge}$=R2*C1) of the capacitor C1 are very different. In a real circuit, the ratio $\tau_{charge}/\tau_{discharge}$ is selected to be approximately 100/1.

Figure 4:
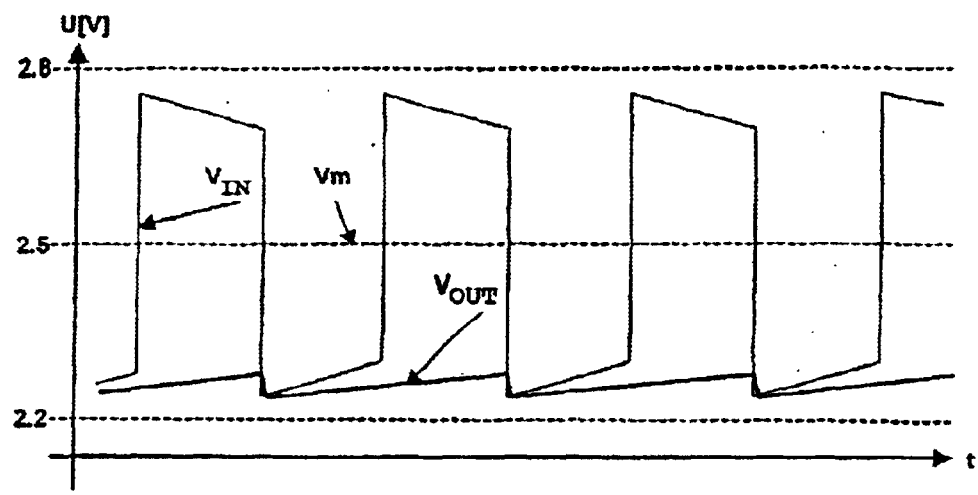
FIG. 4 shows input signals and output signals of the peak value rectifier.

If a square wave alternating voltage $V_{IN}$ of, for example, 500 mVss, which is superimposed on the DC voltage Vm=2.5 V and is dependent on the temperature-dependent internal resistance Ris is then present at the input IN, see FIG. 4, the output signal $V_{OUT}$ will very quickly follow the lower peak value of the input signal $V_{IN}$ and rise again only slowly. A DC (sawtooth) voltage $V_{OUT}$—shown by heavy unbroken lines—which follows the lower peak value of the input voltage Vm+ $V_{IN}$ is thus produced at the output OUT.

The rectifier converts the alternating voltage signal $V_{IN}$= 500 mVss=±250 mV into a DC voltage signal: $V_{OUT}$=−250 mV. Zero crossover point is at Vm=2.5 V. The output signal is therefore on average: Vm−0.250 V=2.250 V.

FIG. 5 shows a known typical circuit design for determining the probe internal resistance by means of a peak rectifier.

The operational amplifiers V2, V3 and V4 are fed with the supply voltage Vcc=5 V in a way which is not illustrated. The operational amplifier V2 forms, with the resistors R10 to R14 and the capacitor C10, a square wave oscillator with an output frequency of approximately 3 kHz.

Figure 8B:
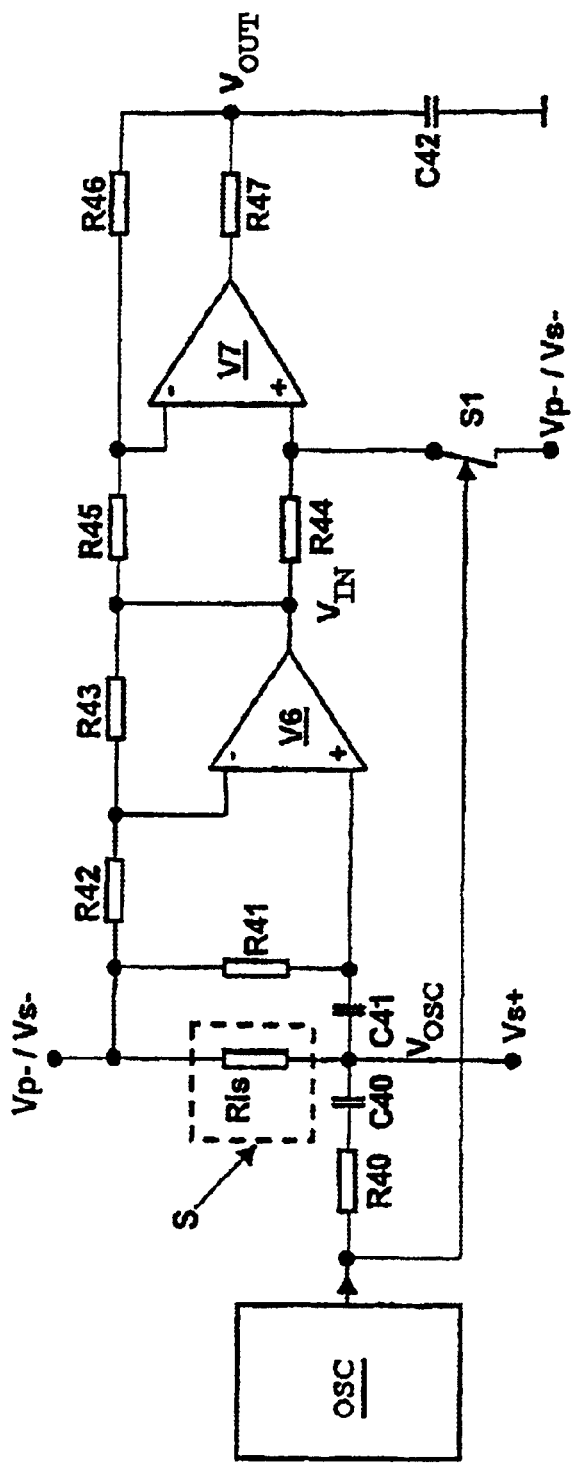
FIG. 8b shows a basic circuit diagram of a circuit according to the invention for determining the probe internal resistance Ris with a synchronous demodulator.
Figure 8A:
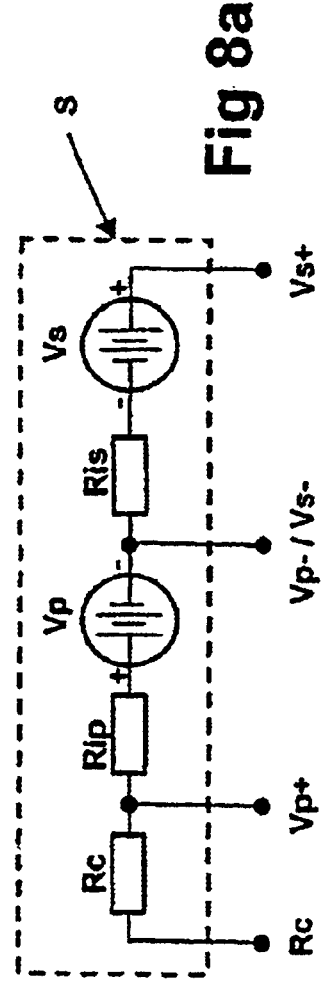
FIG. 8a shows the equivalent circuit diagram of a lambda probe.

The lambda probe S (whose equivalent circuit diagram is illustrated in FIG. 8a) in which the internal resistance Ris to be measured is located is represented as a box formed by dashed lines. The internal resistance Ris is connected to the center voltage Vm=2.5 V, which is the reference potential of the probe and of the subsequent inverting alternating voltage amplifier with a gain factor of approximately 10, which is formed from the operational amplifier V3, the resistors R16 to R18 and the capacitor C12.

The oscillator signal which appears at the output of the operational amplifier V2, an alternating current with approximately 500 μAss, is connected into the probe via the resistor R15 and the capacitor C11. An alternating voltage, which is amplified in the amplifier V3 and rectified in the subsequent peak value rectifier, correspondingly drops across the internal resistance Ris, see also FIGS. 3 and 4 as well as the associated description.

The disadvantages of this circuit have already been mentioned at the beginning: falsification of the output value with a roof-shaped slope of the square wave signal and a high degree of sensitivity to the EMC interference pulses (FIG. 9), due to the rapid response of the rectifier.

According to the invention, this problem is satisfactorily solved in that a synchronous demodulator with integrated filtering means is used for rectification.

As the phase and frequency of the measurement signal (oscillator signal) are known, it is possible to perform rectification under the control of the oscillator signal. This is carried out, for example, by means of an amplifier whose amplification can be switched over between +1 and −1. If the switching over takes place in synchronism with the changing of the positive and negative amplitudes of the oscillator signal, the effect is to rectify the input signal $V_{IN}$ (which is synchronous with the oscillator) with respect to the center voltage Vm. The phase shift between the oscillator signal and input signal is negligible here. If the signal is subsequently also filtered, a DC voltage which corresponds to the average value of the positive amplitude roof of the input alternating voltage is obtained.

Figure 7:
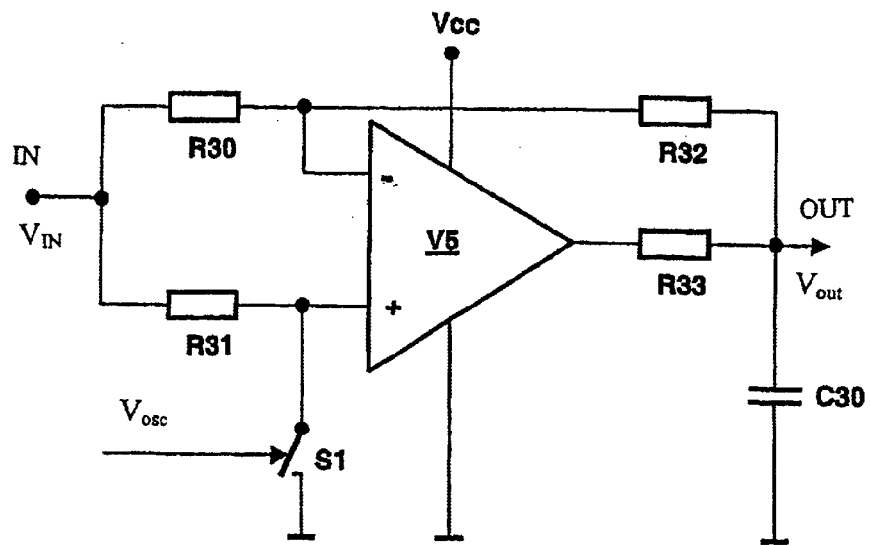
FIG. 7 shows an exemplary embodiment of a synchronous demodulator with integrated filtering means.

FIG. 7 shows an exemplary embodiment of a synchronous demodulator which is known per se and which is composed of an operational amplifier V5, resistors R30 to R33 and a capacitor C30. A switch which is activated by the oscillator signal $V_{OSC}$ is arranged between the non-inverting input of the operational amplifier V5 and the reference potential (0 V). When the switch S1 is opened, the operational amplifier V5 has a gain factor of "+1", and when the switch S1 is closed it is "−1". The output signal $V_{OUT}$ at the output OUT of the circuit follows the output signal of the amplifier V5 with the filter time constant τ=R33*C30 of the filter which is formed from the resistor R33 and the capacitor C30, said constant being, for example, 30 ms.

FIG. 8b shows a basic diagram of a circuit according to the invention for determining the probe internal resistance Ris with a synchronous demodulator with integrated filtering means.

For the sake of better comprehension, an equivalent circuit diagram of a lambda probe S is illustrated in FIG. 8a. Said lambda probe S is composed:

1.) of what is referred to as reference cell, i.e. of the electrodes between the measurement chamber and air, represented in the drawing by the Nernst voltage Vs which can be measured between the electrodes, and the internal resistance Ris of the diffusion barrier between them, 2.) of what is referred to as a pump cell, i.e. of the electrodes between the measuring chamber and exhaust gas, represented by the pump voltage Vp dropping between them and the (reference) resistance Rip between these electrodes, and 3.) of a calibration resistor Rc in the probe plug.

The first to fourth terminals Vs+, Vp−/Vs−, Vp+ and Rc have connections from the lambda probe S.

The operation amplifier V6 and V7 are supplied with the supply voltage Vcc=5 V in a way which is not illustrated in FIG. 8b. The square wave oscillator OSC is indicated as a box but it can in principle be embodied as the circuit which is illustrated in FIG. 5, is constructed around the operational amplifier V2 and has an output frequency of approximately 3 kHz.

The lambda probe S (FIG. 8a) in which the internal resistance Ris to be measured is located between the terminals Vs+ and Vp−/Vs− (at which the center DC voltage Vm=+2.5 V is present) is represented as a box formed from dashed lines.

The oscillator signal which appears at the output of the square wave oscillator OSC is connected into the probe via the resistor R40 and the capacitor C40 as an alternating current with approximately 500 μAss, and fed at the same time to the switch S1. Correspondingly, an alternating voltage drops across the temperature-dependent internal resistance Ris, which alternating voltage is amplified, in a following alternating voltage amplifier V6 which is connected to resistors R40 to R43 and the capacitor C41, to a gain factor of approximately 10 (it will be assumed for example that $V_{IN}$=500 mVss=±250 mV as in FIG. 4), and rectified (with reference to the center voltage Vm) in a synchronous demodulator V7 which follows the alternating voltage amplifier V6 (see FIG. 7) and is composed of an operational amplifier V7, resistors R44 to R47 and a capacitor, and is subsequently filtered by the filter composed of the resistor R47 and capacitor C42.

Figure 6:
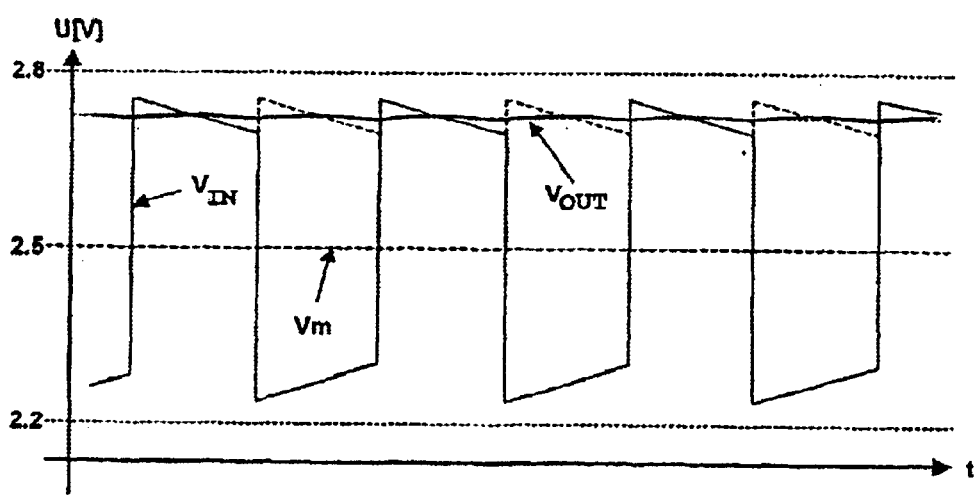
FIG. 6 shows input signals and output signals of the synchronous demodulator with integrated filtering means.

FIG. 6 shows the temperature-dependent square wave signal $V_{IN}$ (for example 500 mVss=±250 mV) which is applied to the input IN of the synchronous demodulator V5 (FIG. 7) or V7 (FIG. 8b) and is superimposed on the center voltage Vm, with a roof-shaped slope of approximately 10%. The synchronous demodulator V5 or V7 rectifies this square wave signal in synchronism with the switching over of the amplification, i.e. the signal element below Vm is mirrored at the line Vm, that is to say folded upward (roof-shaped slopes shown by dashed lines). The output signal of the operational amplifier V5 or V7—the roof-shaped slopes arranged one next to the other—is subsequently filtered and forms, together with the center voltage Vm, the output signal $V_{OUT}$ which follows the upper peak value of the input voltage, shown in FIG. 6 by a heavy unbroken line.

The circuit according to the invention has considerable advantages.

simple, cost-effective design with standard components;
lack of sensitivity to roof-shaped slopes of the input signal;
significantly improved conversion precision;
significantly improved lack of sensitivity to EMC interference pulses (see FIG. 9); and
suitable for integration into integrated circuits.

Figure 9:
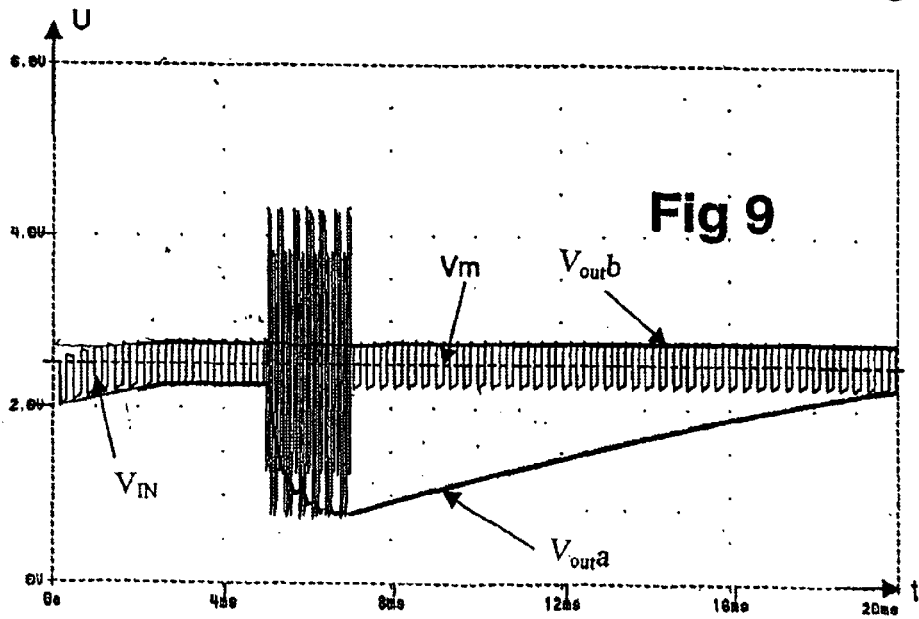
FIG. 9 shows a comparison of the interference sensitivities of the known circuit and of the circuit according to the invention.

The timing behavior of the device according to the invention for measuring the internal resistance Ris of a lambda probe with respect to EMC interference pulses is illustrated in comparison with that of the known device in FIG. 9. In a diagram in whose abscissa direction time t is plotted, and in whose ordinate direction voltages U are plotted, the center (DC) voltage Vm=±2.5 V is represented as a dashed straight line. The temperature-dependent input voltage $V_{IN}$ (for example 500 mVss=±250 mV according to FIGS. 4 and 6) is superimposed on this center voltage Vm. An EMC interference voltage of approximately+2 V around the center voltage Vm should occur for a period of approximately 2 ms, and the behavior of the known device and of the device according to the invention with respect to this EMC interference voltage are indicated.

According to FIGS. 3 to 5 and the associated description, a (sawtooth) DC voltage $V_{OUT}$, which follows the lower peak value of the input voltage Vm+$V_{IN}$ is present at the output of the peak rectifier V1 and V4, respectively. The profile of this voltage $V_{OUT}$ is represented in FIG. 9 as a voltage $V_{OUT}$a shown by a heavy unbroken line. As a result of the ratio of 100/1 between the charge time constant and the discharge time constant of the peak rectifier, this signal also quickly follows the lower peak value of an EMC interference voltage which occurs, which simulates a sudden jump in temperature, but is repeated only very slowly after it ends, as a result of which an incorrect signal, i.e. an incorrect probe temperature, is measured for a relatively long time and the probe heater then reacts incorrectly to this.

The output signal of the device according to the invention is represented as a voltage $V_{OUT}$b shown by a heavy unbroken line. It is apparent from this that the synchronous demodulator cannot be misled by suddenly occurring EMC interference voltages and overall it generates an output signal $V_{OUT}$ which better represents the prevailing probe temperature.

What is claimed is:

1. A device for measuring the internal resistance of a linear lambda probe of an internal combustion engine, having a voltage amplifier for amplifying an alternating voltage which drops across the internal resistance and is brought about by an alternating current applied to the first probe terminal, and having a rectifier for rectifying the amplified alternating voltage, wherein the rectifier is a synchronous demodulator whose voltage amplification can be switched between two predefined values with the frequency of the alternating voltage which drops across the internal resistance, and whose output signal is filtered by means of a filter, and wherein a switch which can be switched with the frequency of the alternating voltage which drops across the internal resistance is arranged between the noninverting input of the synchronous demodulator and a second probe terminal.

2. The device as claimed in claim 1, wherein the predefined values of the voltage amplification of the synchronous demodulator of the values "+1" and "−1".

3. Circuit for measuring the internal resistance of a linear lambda probe comprising:

a voltage amplifier coupled with a resistance which receives a signal having a frequency, a synchronous demodulator receiving the output signal of the amplifier, wherein the voltage amplification of the demodulator is switched between two predefined values according to the frequency of the signal; and a filter for filtering the output signal of the demodulator, wherein the filter comprises a resistance and a capacitance coupled in series between the output of the demodulator and a reference potential.

4. The circuit as in claim 3, wherein the voltage amplifier is a differential amplifier.

5. The circuit as in claim 3, wherein the demodulator comprises an operational amplifier.

6. The circuit as in claim 5, wherein the operational amplifier is coupled with the amplifier through a first and second resistance.

7. The circuit as in claim 3, wherein the predefined values are "1" and "−1", respectively.

8. The circuit as in claim 3, further comprising a switch between a noninverting input of the operational amplifier and a bias voltage.

9. The circuit as in claim 8, wherein the bias voltage is derived from the lambda probe.

10. The circuit as in claim 8, wherein the bias voltage is a mid voltage.

11. Arrangement for determining the fuel/air mixture comprising:

a lambda probe having at least a first and second terminal;

an amplifier having an input coupled with the first and second terminal and an output;

a signal generator for generating a signal having a frequency being fed to the first input of the lambda probe;

a rectifier having an input coupled with the output of the amplifier and an output, wherein the rectifier comprises a demodulator having a selectable amplification which is switched between a first and second value with a frequency controlled by the frequency of the signal; and a filter for filtering the output signal of the demodulator, wherein the filter comprises a resistance and a capacitance coupled in series between the output of the demodulator and a reference potential.

12. The arrangement of claim 11, wherein the demodulator comprises an operational amplifier.

13. The arrangement of claim 11, wherein the first and second values are "1" and "−1", respectively.

14. The arrangement of claim 11, further comprising a switch between a noninverting input of the operational amplifier and the second terminal.

* * * * *